(12) United States Patent
Wireman

(10) Patent No.: US 6,908,502 B2
(45) Date of Patent: Jun. 21, 2005

(54) DEODORIZER MOUNTING

(76) Inventor: Wallace Wireman, 113 Park Ave., Walton, KY (US) 41094

( * ) Notice: Subject to any disclaimer, the term of this patent is extended or adjusted under 35 U.S.C. 154(b) by 0 days.

(21) Appl. No.: 10/337,481

(22) Filed: Jan. 7, 2003

(65) Prior Publication Data

US 2004/0129142 A1 Jul. 8, 2004

(51) Int. Cl.$^7$ ............................................. B01D 53/04
(52) U.S. Cl. ......................... 96/117.5; 96/147; 96/151; 96/152; 96/153; 96/416
(58) Field of Search ............................... 96/108, 117.5, 96/147, 148, 151–153, 414–417; 422/5

(56) References Cited

U.S. PATENT DOCUMENTS

| | | | |
|---|---|---|---|
| 1,975,426 A | | 10/1934 | John |
| 2,439,708 A | | 4/1948 | Abraham |
| 2,557,557 A | * | 6/1951 | Newcum .................... 210/282 |
| 2,691,716 A | | 10/1954 | Wellens |
| 2,765,046 A | * | 10/1956 | Rondholz .................... 62/271 |
| 2,991,517 A | | 7/1961 | Bundy |
| 3,125,407 A | | 3/1964 | Kagan |
| 3,254,784 A | * | 6/1966 | Lancesseur .................. 96/148 |
| 3,841,484 A | * | 10/1974 | Domnick .................... 210/95 |
| 3,966,440 A | * | 6/1976 | Roberts ..................... 96/117.5 |
| 4,133,656 A | * | 1/1979 | Kippel et al. ................ 96/416 |
| 4,306,892 A | | 12/1981 | Atalla |
| 4,523,870 A | | 6/1985 | Spector |
| 4,530,706 A | * | 7/1985 | Jones ........................ 96/117.5 |
| 4,549,250 A | | 10/1985 | Spector |
| 4,676,954 A | | 6/1987 | Wilson |
| 4,714,984 A | * | 12/1987 | Spector ...................... 362/101 |
| 4,726,823 A | * | 2/1988 | Brice ........................... 96/417 |
| 4,840,773 A | | 6/1989 | Wade |
| 4,921,444 A | | 5/1990 | Cama |
| 4,931,224 A | | 6/1990 | Holzner |
| 4,999,034 A | * | 3/1991 | Mager et al. .............. 96/117.5 |
| 5,285,014 A | | 2/1994 | Gilchrist |
| 5,468,447 A | * | 11/1995 | Bermas ......................... 422/5 |
| 5,478,505 A | | 12/1995 | McElfresh |
| 5,505,753 A | * | 4/1996 | Heysek ........................ 96/416 |
| 5,624,478 A | * | 4/1997 | Patapanian et al. ........... 96/108 |
| 5,820,792 A | | 10/1998 | Lin |
| 6,190,440 B1 | * | 2/2001 | Purnell ........................ 96/108 |
| 6,264,887 B1 | * | 7/2001 | Farmer ......................... 422/5 |
| 6,346,143 B1 | * | 2/2002 | McGowan ................. 96/117.5 |
| 6,413,302 B1 | * | 7/2002 | Harrison et al. ............... 96/63 |
| 6,497,756 B1 | * | 12/2002 | Curado et al. ............. 96/117.5 |
| 2002/0131888 A1 | * | 9/2002 | Zobele et al. .................. 422/5 |
| 2003/0029320 A1 | * | 2/2003 | Janisch et al. ............. 96/117.5 |
| 2003/0064002 A1 | * | 4/2003 | Jaworski et al. .............. 422/28 |
| 2003/0124022 A1 | * | 7/2003 | Georges et al. ................ 422/5 |

* cited by examiner

Primary Examiner—Robert H. Spitzer
(74) Attorney, Agent, or Firm—Frost Brown Todd LLC

(57) ABSTRACT

A deodorizer mounting for engagement into a wall-mounted electrical outlet box including an adsorber unit for removing gases and odors from the ambient atmosphere, a generally L-shaped bracket including a horizontal leg and a vertical leg, a cover plate having a front side and a rear side, at least one prong, mounted to and extending perpendicularly from the rear side of the cover plate, sized and spaced to engage the female receptacle of the electrical outlet box, and a means to affix the front side of the cover plate to the vertical leg of the L-shaped bracket. A mounting device and method of installation obviates or at least reduces the poor aesthetics of conventional wall-mounted adhesive units and the relatively high replacement costs for non-securable room deodorizers.

10 Claims, 4 Drawing Sheets

DEODORIZER MOUNTING

BACKGROUND OF THE INVENTION

The present invention relates to mounting and more particularly to non-electrical devices for mounting room deodorizers.

Non-electrical devices for mounting room deodorizers of the conventional type generally comprise wall-mounted adhesive units, self standing units, or grille engaged units where a fastening clip, u-shaped hook, or spring engaged flat tongs adapted for gripping are utilized to engage an automobile grille, closet ledge, or refrigerator shelf to locate the room deodorizer.

Generally there are a number of problems with using the aforementioned units not the least of which involve the relatively poor aesthetics which result from removing the wall-mounted adhesive unit from the building wall or window, and the associated repair costs. In the case of the stand-alone or grille/ledge/shelf gripped units, aesthetics are not an issue since the equipment is either not installed or installed using an easy-to-remove "clip-on" method, and are generally in a location which does not detract from the other aesthetics; however, in commercial lodging and hospital settings, the lack of secureness and permanency of the units, and the ease in removal of these units, lead to exorbitant costs due to constant replacement requirements. The units placed in public facilities tend to "walk away" without more secure methods of mounting. The present invention addresses these concerns. Further, the fact that the present invention does not utilize electricity provides additional cost savings.

BRIEF SUMMARY OF THE INVENTION

The present invention provides a mounting device for deodorizers and a method of installation which eliminates or at least reduces the poor aesthetics of conventional wall-mounted adhesive units and the relatively high replacement costs for non-securable room deodorizers.

The present invention provides an integrated deodorizer mounting device which has improved operating efficiency over conventional deodorizing systems.

In one form, the invention provides a deodorizer mounting device for engagement into a wall-mounted electrical outlet in which the outlet is optionally located near floor level, and the mounting device includes a cover plate having a front side and a rear side.

Preferably, the deodorizer mounting device includes a generally L-shaped bracket having a horizontal leg and a vertical leg, in which the horizontal leg is attached to the adsorber unit and the vertical leg to the cover plate; at least one non-electrical prong, sized and spaced to engage the female receptacle of an electrical outlet, mounted to and extending perpendicularly from the rear side of the cover plate.

Preferably, the deodorizer mounting device includes a means to moveably (in a swiveling manner) affix the front side of a cover plate to the vertical leg of the adsorber unit.

Preferably, the L-shaped bracket is attached to the adsorber unit.

Preferably, the cover plate is affixedly attached to the L-shaped bracket on a vertical surface.

In a further form, the invention provides a deodorizer mounting device wherein said cover plate and said prong are electrically non-conductive.

Preferably, the deodorizer mounting device, when engaged with the wall-mounted electrical outlet box, is configured to obstruct only one socket of the outlet box.

Preferably, the cover plate is ovalar shaped and allows said L-bracket to swivel horizontally or vertically.

In a still further form, the invention provides a deodorizer mounting device for location on a wall of a room and the cover plate incorporates a slotted hole for receiving a screw means to affix the mounting device to the wall-mounted electrical outlet box.

In yet another form, the invention provides a wall mounted block to simulate a wall-mounted electrical outlet box, to provide additional non-electrical mounting locations.

BRIEF DESCRIPTION OF THE DRAWING

In order that the invention may be more readily understood, particular embodiments will now be described with reference to the accompanying drawings wherein.

These drawings are intended to be exemplary of the present invention, and not limiting thereof. In these drawings, common numbering refers to the same element in each figure.

DETAILED DESCRIPTION OF THE INVENTION

Figure 1:
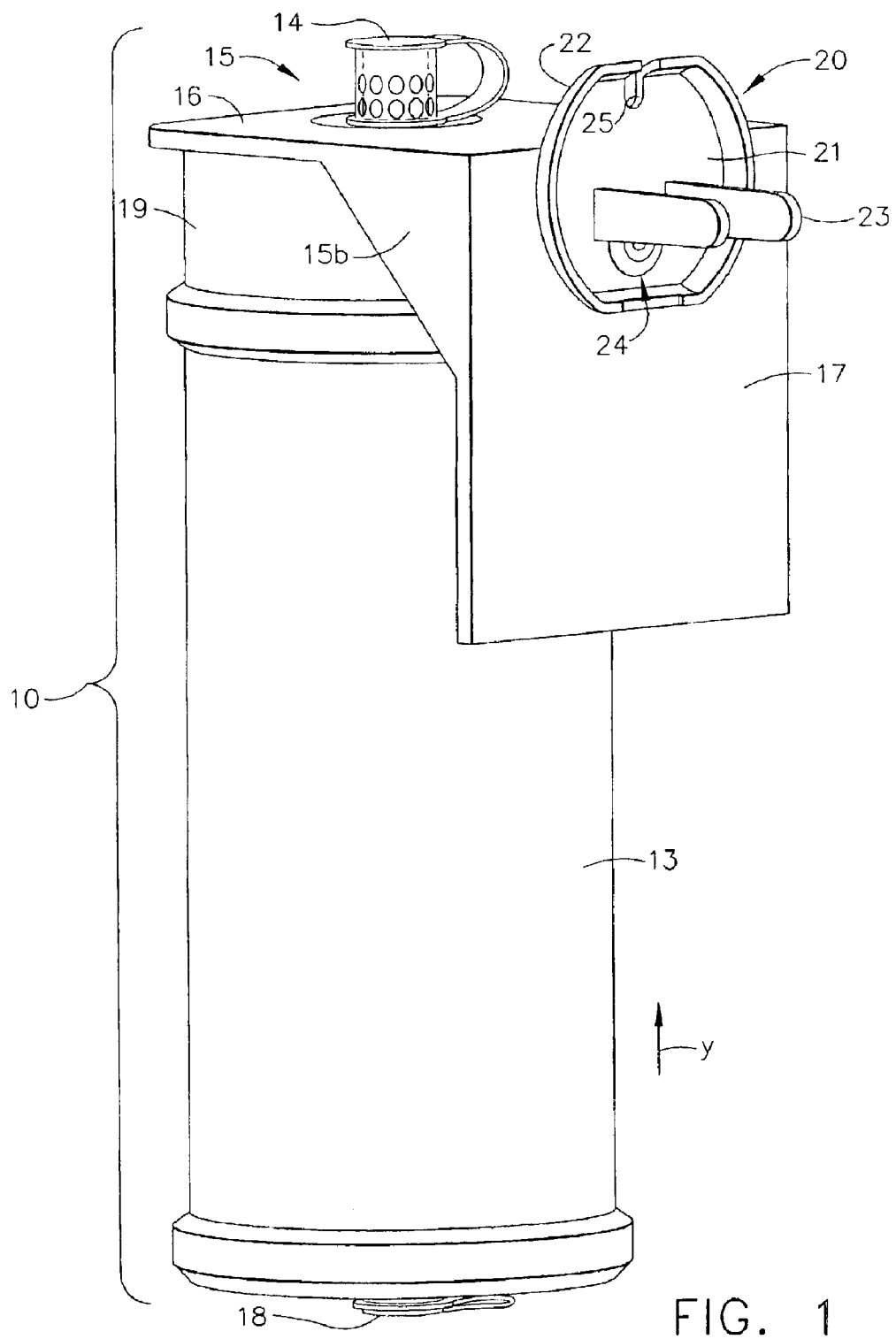
FIG. 1 is a perspective view of a deodorizer mounting device in accordance with the present invention, as seen from the rear face.
Figure 7:
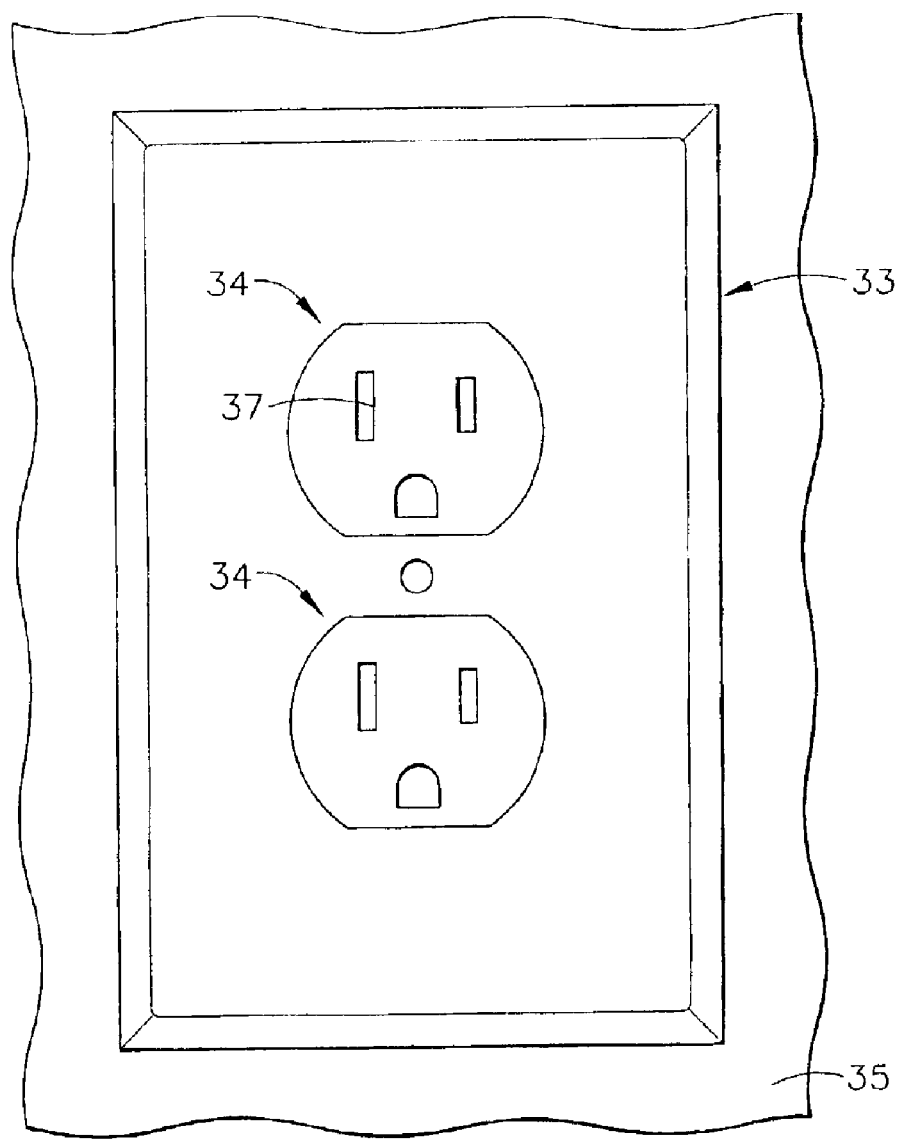
FIG. 7 is a suitable wall-mounted electrical outlet box for accommodating the device.

With reference to the drawings, and more particularly FIG. 1, the deodorizer mounting device 10 according to this embodiment is adapted to engage and fit into a wall-mounted electrical outlet box 33 (FIG. 7) in a wall 35.

As is evident in FIG. 1, the deodorizer mounting device 10 comprises a cover plate 20, a swivel means 24, an adsorber unit 13, a generally L-shaped bracket 15 with a horizontal leg 16 and a vertical leg 17, and at least one prong 23.

The deodorizer mounting device of the present invention differs from the conventional deodorizer mountings described above as is shown more clearly in FIGS. 2, 3 and 4.

Figure 2:
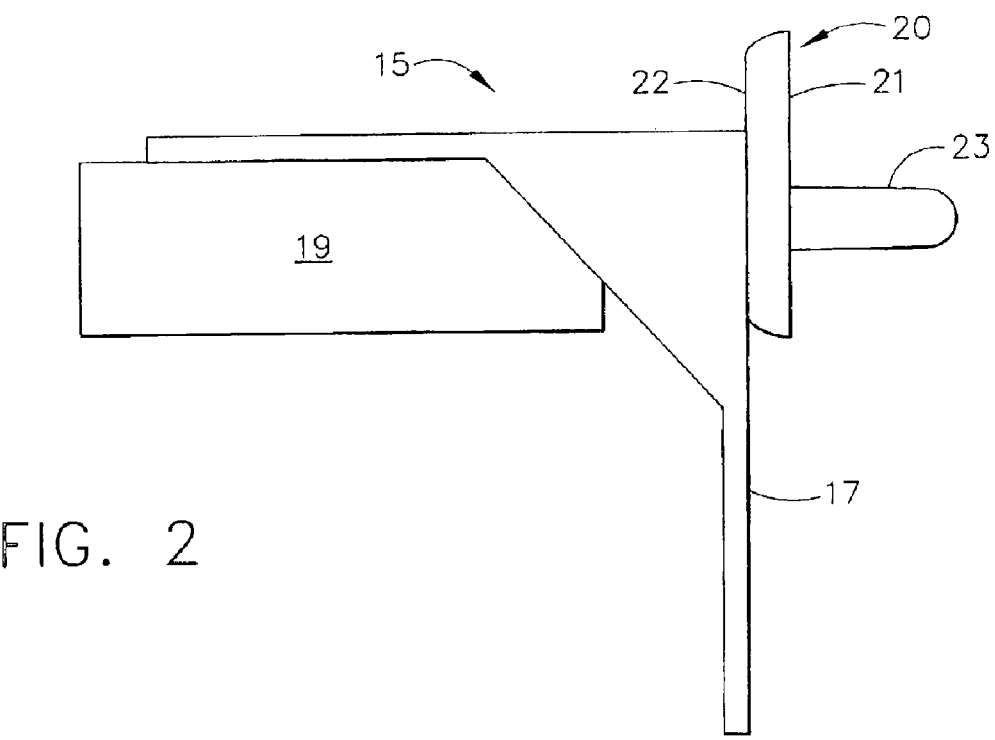
FIG. 2 is a sectional side elevation of the deodorizer mounting device of FIG. 1 showing the main components.
Figure 3:
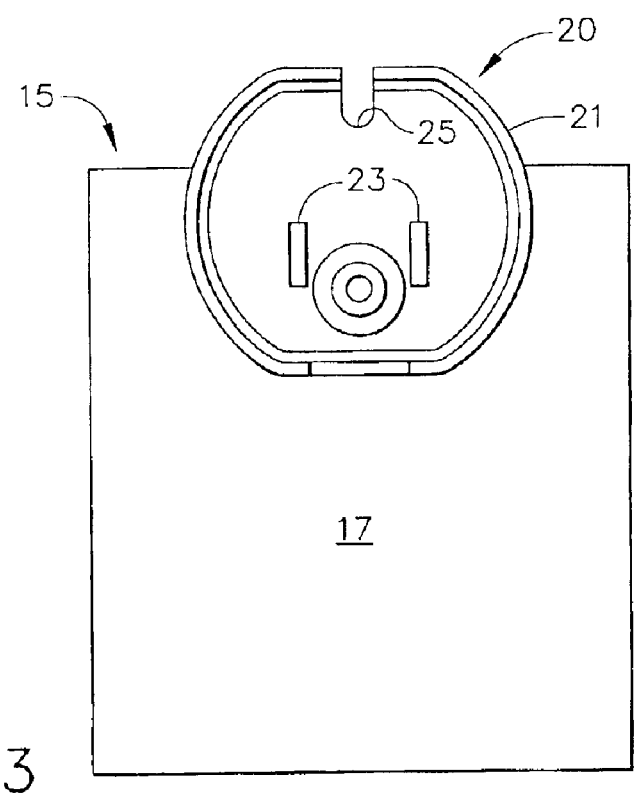
FIG. 3 is a perspective rear view of the deodorizer mounting device of FIG. 2 showing the main components.

Referring particularly to FIGS. 2 and 3, in which a preferred embodiment of the subject invention is shown, the cover plate 20 of the deodorizer mounting device 10 according to the invention has a width which is generally equivalent to that of a wall-mounted electrical socket 34, about 25 mm. The length is about the same size as the width, for example, about 25 mm. Generally, the width extends in a direction perpendicular to the y-direction, as shown on FIG. 1.

The cover plate 20 has a rear surface 21 and a front surface 22. At least one prong 23 is mounted to and extends perpendicularly from the rear side 21 of the cover plate 20 (i.e., perpendicular and outwardly from the plane of the cover plate). The prong 23 is sized and spaced to engage the female receptacle 37 of the electrical outlet box 33. The front side 22 of the cover plate 20 is attached to the vertical leg 17 of the L-shaped bracket 15. This attachment is preferably made by a swivel means 24.

Figure 4:
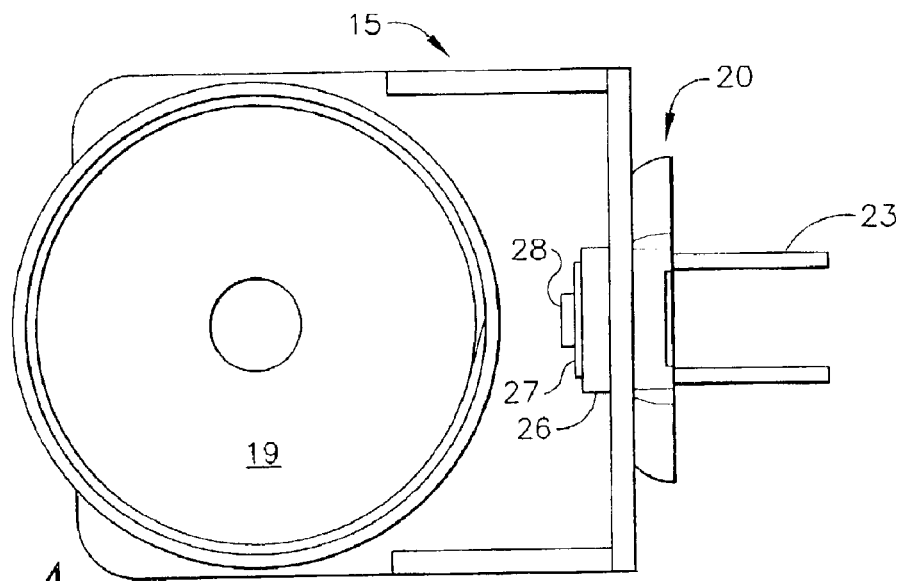
FIG. 4 is a top view of the deodorizer mounting device showing the cap, swivel means and cover plate.

The device is intended to have horizontal or vertical orientation options by a swivel means, generally indicated at 24. The precise nature of the swivel means 24 does not constitute a limitation of the present invention. Any appropriate, commercially available swivel means can be used. It has been found that excellent results are achieved using a rubber gasket 26, metal ring 27 and pierced metal divot 28, as seen in FIG. 4.

The adsorber unit 13 may be facing up, down or to either side, depending on the swivel and the orientation of the outlet box 33. This allows maximum options in placing the device in tight places. Generally, this means that the deodorizer mounting device's cover plate 20 can be slid into either of the aforementioned electrical sockets 34 without the need to pre-orient the deodorizer mounting device 10 to a particular socket 34. Therefore, once a suitable wall-mounted electrical outlet box 33 is decided on, according to this invention, a skilled tradesman is not required for installation purposes. In other words, the consumer is able to slide the deodorizer mounting device 10 into the outlet box 33, fix it in position, horizontally or vertically, and secure it into the electrical outlet box 33 with a screw means through the slotted hole 25 of the cover plate. Any appropriate, commercially available security theft-resistant screw means can be used. It has been found that excellent results are achieved using a thumb nail screw inserted into the slotted hole 25 of the cover plate. As will be evident, it is a "do-it-yourself" (DIY) installation.

In a preferred embodiment, the adsorber unit 13 comprises a container having within it a bed of particulate odor and gas absorbing material, for example, a molecular sieve. A tubular passage extends through the container and bed and is provided with a perforated peripheral wall adjacent the bed. The bed is fully enclosed except at the perforated tube wall. Air containing moisture, gases and odors is directed through the tubular passage. The molecular sieve bed has an affinity for gases and odors and an affinity for moisture as well. By directing the air through the tubular passage, rather than directly through the bed itself, more of the gases and odors and less moisture will be absorbed by the bed, increasing the working life of the bed. This effect may be further improved if the tubular passage is provided with diffuser material such as baffles, polyester, or fiberglass to slow down and disperse the air passing therethrough. The tubular passage is preferably closed off on both ends with adjustable plugs, 14 and 18. The molecular sieve bed preferably contains indicator particles which change color when the bed needs to be changed. To this end, the container is preferably transparent allowing visual inspection of the bed. Further, the container preferably has an access device suitable for refilling the molecular sieve bed and a cap 19 at one end of the top of the adsorber 13. Adjusting the plug at the top 14 or bottom 18 of the perforated tubular passage extends the longevity of the molecular sieve.

A generally L-shaped bracket 15 includes a horizontal leg 16 and a vertical leg 17. The horizontal leg 16 extends horizontally outwardly from the adsorber unit 13 and is attached to the cap 19 of the adsorber unit 13. The vertical leg 17 extends vertically in a direction generally perpendicular to the direction of the cover plate prong 23 and the horizontal leg 16. This L-shaped bracket 15 provides a support surface for the cover plate and its vertical leg 17 supports the unit's placement in the socket 34. Moreover, the wedge portion 15b between the side 17 and bottom 16 legs is designed to provide significant resilience to prevent buckling of the L-shaped bracket even when the unit is removed from the electrical outlet box for filling or for changing locations.

Figure 5:
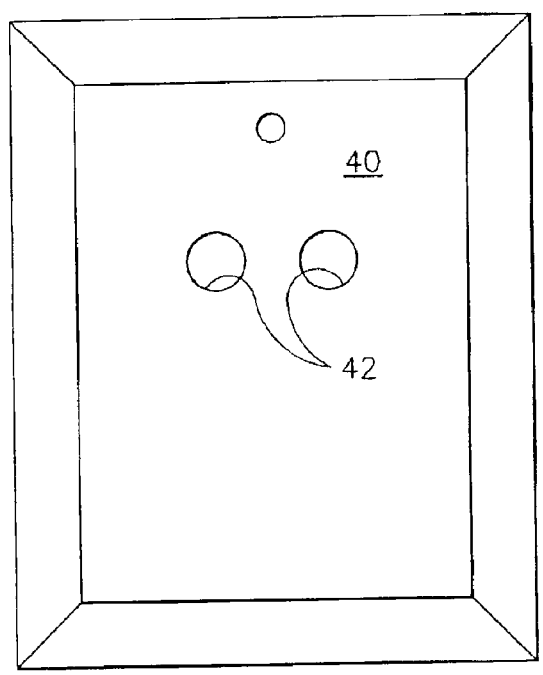
FIG. 5 is a perspective view of the non-electrical block for accommodating the device.
Figure 6:
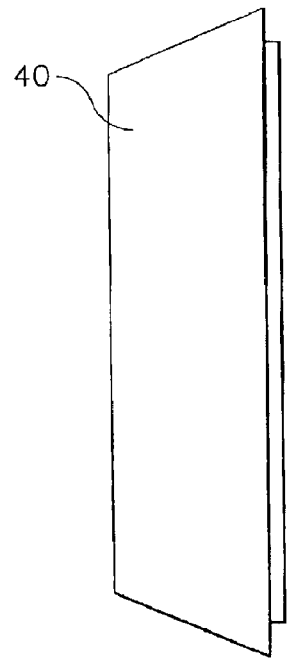
FIG. 6 is a back view of the non-electrical block.

Referring now to FIGS. 5 and 6, a further option for mounting would comprise a block 40 with non-electrical attachment means (for example, adhesive), designed and shaped with engagement openings 42 to simulate an electrical outlet box, for mounting the deodorizer mounting device 10 to surfaces where no outlets are present. The block 40 is placed in any desired location and the engagement openings 42 receive the prong 23 as the device 10 is mounted. Particularly for use on, but in no way limited to, home and office walls, clothes or work closets, boats, semi-truck cabs, taxis, and automobiles.

It should be apparent from the above that the deodorizer mounting device of the present invention provides a number of improvements over conventional mounting devices. For example, the easy installation method facilitated by a non-electrical prong, coupled with the security theft-resistant fastening screw means provides that the mounting device is advantageously theft deterrent and not "unconsciously" removed from its location. The building or homeowner need not provide any particular electrical outlet aperture suitable for the deodorizer mounting device, as the alternative non-electrical block may also be used. Furthermore, the compact design of the unit 10 (about 20–80 mm length and width, about 80–170 mm height, for example) wherein the various components are displaced generally vertically relative to each other, enables the deodorizer mounting device to be non-obtrusively utilized. Accommodating the deodorizer mounting device can be readily completed and once the deodorizer mounting device is installed in the outlet box 33 or block 40, its swivel means will accommodate surface area needs.

Although the deodorizer mounting device 10 has been illustrated and described in connection with a particular type of gas and odor adsorbing unit (adsorber 13), it may be of other configurations to accord with other designs of adsorbers, absorbers, deodorizers and the like.

It should also be apparent to those skilled in the art that modifications may be made to the embodiment described above without departing from the spirit or scope of the invention. For example, the dimensions given in relation to the preferred embodiment are preferments only and could easily be varied to suit different electrical sockets and equipped with different brackets to suit different sized adsorber or deodorizer units. Additionally, the width and height of the cover plate 20 may be varied whilst maintaining the prong relationship to the outlet box. Fastening means, which may take many different forms, are provided on the deodorizer mounting device for the purpose of attaching it to electrical outlet box. Because the deodorizer mounting device is optionally located at floor level to capture pet odors and the like, and because the deodorizer mounting device 10 can be mounted vertically or horizontally, there are no major changes required in order to slip the deodorizer mounting device into the receptacle and "plug" it in.

While a specific embodiment of the invention has been shown and described, it will be obvious to those very skilled in the art that various changes and modifications may be made therein, without departing from the scope, spirit and intent of the invention as set forth in the appended claims.

What is claimed is:

1. A mounting device for removably locating a deodorizing unit into a wall-mounted electrical outlet box having at least one female receptacle for receiving a male plug, comprising:
   an adsorber unit for removing gases and odors from the ambient atmosphere;
   a generally L-shaped bracket including a horizontal leg and a vertical leg, each of said legs having a front side and a rear side, said horizontal leg being attached to said adsorber unit;
   a cover plate having a front side and a rear side attached at the front side of said vertical leg of said L-shaped bracket; and
   at least one prong, mounted to and extending perpendicularly from the rear side of said cover plate, sized and spaced to engage the at least one female receptacle of the electrical outlet box.

2. A mounting device in accordance with claim 1, wherein said cover plate is swiveledly attached to said L-shaped bracket on a vertical surface.

3. A mounting device in accordance with claim 1, wherein said cover plate and said at least one prong are electrically non-conductive.

4. A mounting device in accordance with claim 1, wherein said cover plate is ovalar shaped.

5. A mounting device in accordance with claim 1, wherein the attachment of said cover plate and said L-shaped bracket allows said L-shaped bracket to swivel horizontally or vertically.

6. A mounting device in accordance with claim 1, configured to obstruct only one socket of a standard wall-mounted electrical outlet box having at least 2 sockets wherein each socket comprises at least one female receptacle for receiving a male plug.

7. A mounting device in accordance with claim 2 and further comprising, a slotted bole in said cover plate for receiving a screw means to affix said mounting device to said wall-mounted electrical outlet box.

8. A mounting device in accordance with claim 1 wherein said adsorber comprises: a canister comprising a bed of molecular sieve, at least one tubular passage extending through said molecular sieve and being connected to the ambient atmosphere at opposite ends of said canister, said passage being defined by a peripheral foraminous wall, said molecular sieve being exposed to said ambient atmosphere only at said foraminous wall and means to cause a flow of said ambient atmosphere to pass through said tubular passage, whereby gases, odors and a minimum of moisture is adsorbed by said molecular sieve from said ambient atmosphere passing through said passage, and an opening in said adsorber unit for placing an adsorbing portion of said unit in communication with the ambient atmosphere.

9. A mounting device in accordance with claim 8 wherein said molecular sieve bed contains indicator particles which change color when the bed needs to be changed.

10. A mounting device in accordance with claim 9 wherein said molecular sieve bed is longevity-adjustably operated with at least two plugs attached to said tubular passage.

* * * * *